United States Patent
Attygalle et al.

(10) Patent No.: US 9,147,566 B2
(45) Date of Patent: Sep. 29, 2015

(54) METHOD FOR PRODUCING GAS-PHASE METAL ANIONS

(75) Inventors: Athula Buddhagosha Attygalle, Hoboken, NJ (US); Carl S. Weisbecker, New York, NY (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 582 days.

(21) Appl. No.: 13/581,756

(22) PCT Filed: Mar. 23, 2011

(86) PCT No.: PCT/US2011/029636
§ 371 (c)(1),
(2), (4) Date: Oct. 23, 2012

(87) PCT Pub. No.: WO2011/119740
PCT Pub. Date: Sep. 29, 2011

(65) Prior Publication Data
US 2013/0053542 A1 Feb. 28, 2013

Related U.S. Application Data

(60) Provisional application No. 61/317,079, filed on Mar. 24, 2010.

(51) Int. Cl.
| | |
|---|---|
| *H01J 27/02* | (2006.01) |
| *H01J 49/10* | (2006.01) |
| *C23C 26/00* | (2006.01) |
| *C07K 1/107* | (2006.01) |
| *H01J 49/04* | (2006.01) |
| *G01N 33/68* | (2006.01) |
| *B01J 19/08* | (2006.01) |
| *H01J 49/00* | (2006.01) |
| *B01J 12/00* | (2006.01) |

(52) U.S. Cl.
CPC ........ *H01J 49/0459* (2013.01); *G01N 33/6848* (2013.01); *B01J 12/002* (2013.01); *B01J 19/08* (2013.01); *B01J 2219/0896* (2013.01); *G01N 2560/00* (2013.01); *H01J 49/004* (2013.01); *H01J 49/005* (2013.01); *H01J 49/0045* (2013.01); *H01J 49/0072* (2013.01); *H01J 49/0077* (2013.01); *H01J 49/0095* (2013.01)

(58) Field of Classification Search
CPC . H01J 49/0459; H01J 49/004; H01J 49/0045; H01J 49/005; H01J 49/0072; H01J 49/0077; H01J 49/0095; G01N 33/6848; G01N 2560/00; B01J 12/002; B01J 19/08; B01J 2219/0896

See application file for complete search history.

(56) References Cited

U.S. PATENT DOCUMENTS

| | | |
|---|---|---|
| 5,662,913 A | 9/1997 | Capelli |
| 6,555,630 B1 | 4/2003 | Chen et al. |
| 6,756,119 B1 | 6/2004 | Clough |
| 2006/0186331 A1 | 8/2006 | Hartmer et al. |
| 2006/0217508 A1 | 9/2006 | Schmid et al. |
| 2006/0219898 A1 | 10/2006 | Mcluckey et al. |

FOREIGN PATENT DOCUMENTS

WO    WO 2011/119740    9/2011

OTHER PUBLICATIONS

Gillen, Greg et al. "Negative cesium sputter ion source for generating cluster primary ion beams for secondary ion mass spectrometry analysis." J. Vacuum Sci. & Tech. A (2001) 19 568-575.*
Kim, Hugh I. et al. "Cluster phase chemistry: Gas-phase reactions of anionic sodium salts of dicarboxylic acid clusters with water molecules." J. Phys. Chem. A (2006) 110 7777-7786.*
International Search Report and Written Opinion regarding International (PCT) Application No. PCT/US2011/029636, mailed May 26, 2011.
Attygalle et al., "Mild route to generate gaseous metal anions", Rapid Commun. Mass Spectrom., vol. 25, (2011) pp. 681-688.
Coon et al., "Anion dependence in the partitioning between proton and electron transfer in ion/ion reactions", International Journal of Mass Spectrometry, vol. 238 (2004) pp. 33-42.
Kebarle, "A brief overview of the present status of the mechanisms involved in electrospray mass spectrometry", Journal of Mass Spectrometry, vol. 35 (2000), pp. 804-817.
Kebarle et al., "On the mechanisms by which the charged droplets produced by electrospray lead to gas phase ions", Analytica Chimica Acta, vol. 406, (2000), pp. 11-35.
Labowsky et al., "A continuum model for ion evaporation from a drop: effect of curvature and charge on ion solvation energy", Analytica Chimica Acta, vol. 406 (2000) pp. 105-118.
Syka et al., "Peptide and protein sequence analysis by electron transfer dissociation mass spectrometry", PNAS, vol. 101, No. 26 (Jun. 29, 2004), pp. 9528-9533.
Wang et al.; "Charged residue versus ion evaporation for formation of alkali metal halide cluster ions in ESI", Analytica Chimica Acta, vol. 406, (2000), pp. 53-65.

* cited by examiner

*Primary Examiner* — Christopher A Hixson
(74) *Attorney, Agent, or Firm* — Greenberg Traurig, LLP (57) ABSTRACT

Monatomic metal anions are generated in the gas phase by collision-induced dissociation of the anions [26] of a dicarboxylic acid salt of the metal. This method is applicable to a number of metals, including sodium, potassium, cesium, and silver. The metal anions produced in this way can subsequently be stored in an ion trap [88] or transmitted as a focused beam [52]. The metal anions of this invention undergo collisional cooling and have low kinetic energy, which distinguishes them from ions produced by other high energy processes (with kinetic energy in excess of 1 keV). Metal anions so produced can be used to pattern nanoscale features on surfaces [56], used as electron transfer agents or reducing agents in ion-molecule reactions, or used for surface [122] modification of biomaterials [124].

15 Claims, 9 Drawing Sheets

METHOD FOR PRODUCING GAS-PHASE METAL ANIONS

CROSS-REFERENCE TO RELATED APPLICATIONS

The present application is a §371 conversion of International (PCT) Application No. PCT/US2011/029636, filed on Mar. 23, 2011, which is incorporated by reference herein in its entirety, and further claims the benefit of U.S. Provisional Patent Application No. 61/317,079, filed Mar. 24, 2010, which is incorporated by reference herein in its entirety.

STATEMENT REGARDING FEDERALLY SPONSORED RESEARCH

Not applicable.

FIELD OF THE DISCLOSURE

The present disclosure pertains to the field of generating gas-phase ions and, more specifically, to a method for generating gas-phase metal anions that have low kinetic energies and are suitable for use in mass spectrometry, chemical synthesis, imaging and patterning of nanoscale surface features.

BACKGROUND OF THE INVENTION

Prior to the present disclosure, methods were known for generating metal anion beams with high kinetic energies (e.g., kinetic energies in a range of 1-1000 keV). However, for numerous processes, it would be desirable to have access to low-energy gas-phase metal anions generated under mild conditions. As used herein, "mild" refers to conditions that do not impart a large excess of kinetic energy to the anion beyond the energy needed to produce it. In the field of mass spectrometry, processes operating under such conditions may also be referred to as "soft", as opposed to "hard", ionization processes. A practical reason for preferring mild (or "soft") processes is that the ions formed from such processes often exhibit a different gas-phase chemistry than those produced under more energetic (or "hard") processes. A method for efficiently generating low-kinetic-energy metal anion beams using bench-top laboratory equipment has potential applications for the production of nanoscale materials, for the production of reagent ions to induce chemical transformations in gas phase-microreactors, for surface analysis, for imaging science, for medical research, and for uses in other areas of science and engineering. For example, metal ion beams are essential for applications in the field of accelerator mass spectrometry for the analysis of rare isotopes and trace elements. Gas-phase anions with low electron affinities (e.g., alkali metal anions, or "alkalides") also have important applications as electron transfer agents in an emerging technique for protein structure elucidation called electron transfer dissociation (ETD). The production of alkali metal anions is also a required first step for some nuclear physics research experiments.

BRIEF SUMMARY OF THE DISCLOSURE

The present disclosure addresses a process for producing monatomic gas-phase metal anions having low kinetic energies. In one aspect, the invention comprises a process for producing monatomic gas-phase metal anions from organic salts of the metal. In an embodiment of this process, the organic salt is a metal dicarboxylate salt. In an embodiment of this process, a conventional electrospray ionization ("ESI") source is used to generate a nebulized spray of charged droplets containing dicarboxylate anions and metal cations from a solution of a metal dicarboxylate salt in a solvent or a mixture of solvents. Singly-charged metal dicarboxylate anions generated by the ESI source are selected in an electromagnetic separation step, and dissociated in a collision cell to form anions of the metal. The metal anions are isolated from among other reaction products in a second electromagnetic separation step, and collimated into a beam of metallic anions.

In a second aspect of the invention, a method of patterning nanoscale structures onto a substrate includes the step of impacting a beam of gas-phase metal anions onto a surface of the substrate, and moving the substrate so that the gas-phase metal anions are deposited on the surface in a pre-determined pattern.

In a third aspect of the invention, a method of elucidating the structure of a large molecule includes a step of impacting a beam of gas-phase metal ions into a sample of the large molecules, and analyzing the resulting charged fragments and radical fragments of the of the large molecule by means of a mass spectrometer. In an embodiment of this third aspect, the large molecule is a protein.

In a fourth aspect of the invention, a method of modifying a surface of a material includes steps of passing a beam of gas-phase metal anions through an aperture to diverge the beam, and impacting the diverged beam onto the surface of the material, thereby uniformly depositing the metal onto the surface. In an embodiment of this fourth aspect, the metal is silver and the material is a biomaterial for implantation in a human body.

BRIEF DESCRIPTION OF FIGURES

For a better understanding of the present invention, reference is made to the following detailed description of the exemplary embodiments considered in conjunction with the accompanying drawings, in which.

DETAILED DESCRIPTION OF THE INVENTION

In an embodiment of the present invention, a process for generating gas-phase metal anions, which is referred to herein after as the "dicarboxylate process", can efficiently generate metal anion beams with low kinetic energy using bench-top laboratory equipment. The procedure provides a new mild route for generating gas-phase metal anions, such as $Na^-$, $K^-$, $Cs^-$, and $Ag^-$, by collision-induced dissociation (CID) of the singly-charged anions of their dicarboxylic acid salts $[A+M]^-$. Metals suitable for producing gas-phase metal anions according to a method of the present invention include those that form monovalent cations in aqueous solution with the selected dicarboxylic acid. Such metals include sodium, potassium, cesium, silver, copper, cobalt, gold, thallium, gallium, and indium.

In an embodiment of the present invention, the dicarboxylate salt is a salt of oxalic acid (i.e., a metal oxalate salt.) In other embodiments of the invention, metal anions are produced from the singly-charged anions of other dicarboxylic acid salts, including, but not exclusively limited to, metal salts of maleic acid, fumaric acid, succinic acid, malonic acid, malic acids, tartaric acids, glutamic acids and aspartic acids.

In an embodiment of a process according to the present invention, a metal dicarboxylate salt is dissolved in a polar solvent or a mixture including a polar solvent. Suitable polar solvents include, but are not limited to, water, acetonitrile, and methanol. A mixture of solvents that may be used advantageously comprises one part water blended with one part acetonitrile or methanol. In various embodiments of the process, the concentrations of metal cation and dicarboxylic acid dianion dissolved in the solution are in a range of 0.1-1.0 mM. A pH modifier may be added to this solution to adjust the solution pH to optimize production of the desired precursor anions.

Figure 1:
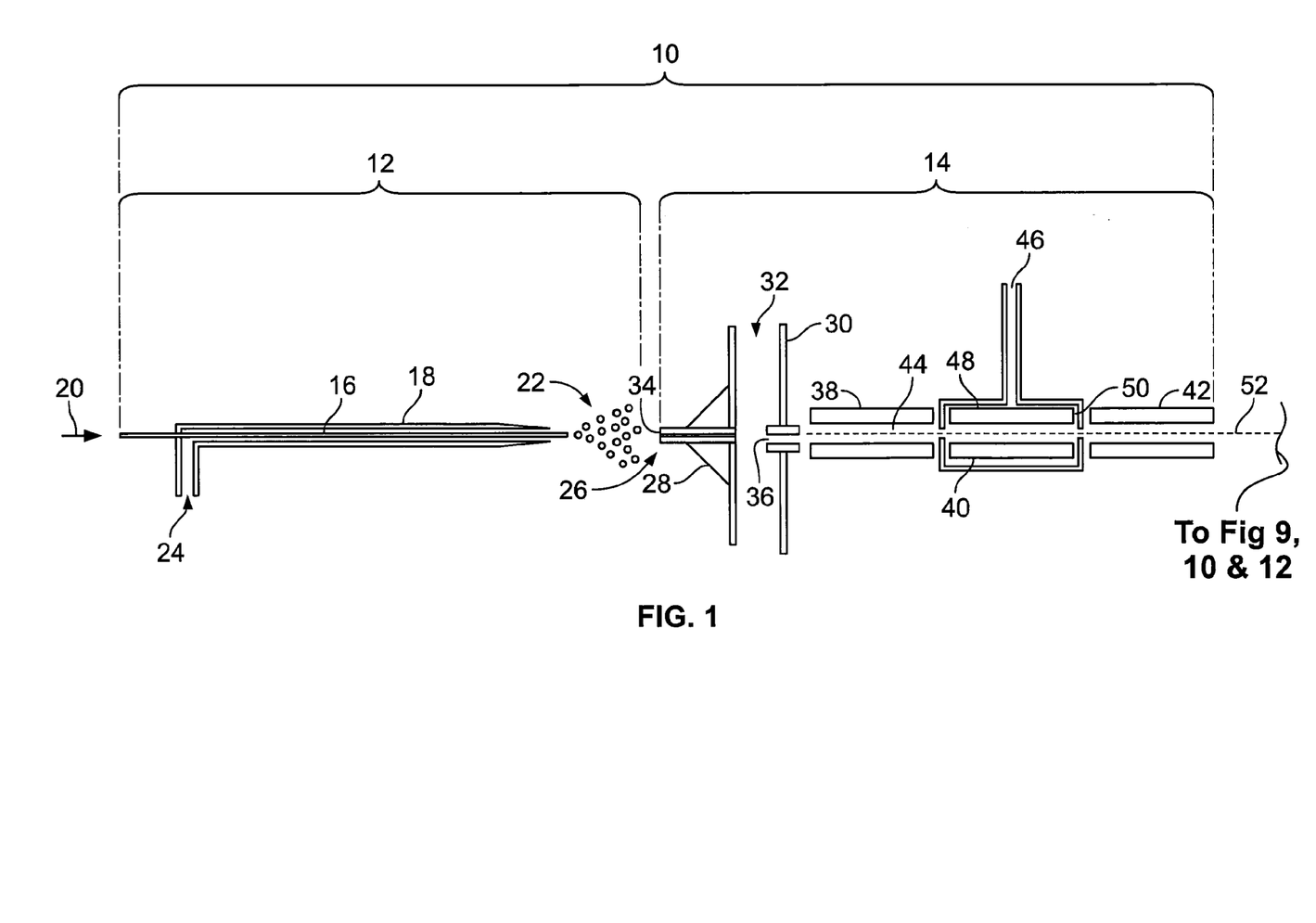
FIG. 1 is a schematic diagram of an electrospray ionization device hyphenated to a triple quadrupole mass spectrometer useful for producing monatomic metal anions with low kinetic energy in a process according to an embodiment of the present invention.

FIG. 1 is a schematic diagram of an assembly 10 comprising an electrospray ionization (ESI) device 12 hyphenated to a triple quadrupole mass spectrometer 14. The assembly 10 may be used to produce a collimated beam of monatomic metal anions with low kinetic energies from electrosprayed metal dicarboxylate salt solutions by a process in accordance with an embodiment of the present invention. The process may be described in two stages, with the operation of the ESI device 12 being the first stage and the operation of the mass spectrometer 14 being the second stage.

The first stage of the process is carried out using an ESI device, such as the ESI device 12 of FIG. 1. The ESI device 12 includes a metal capillary 16 at least partially surrounded by a tube 18. In a process of preparing metal anions according to an embodiment of the present invention, a solution 20 of a metal dicarboxylate salt is pumped through the metal capillary 16 at a flow rate sufficient to provide an optimized, stable, high yield of precursor $[A+M]^-$ anions. For example, the flow rate of the solution 20 may be fixed in the range of 1-10 μL $min^{-1}$. A high negative voltage within the range of about 1 kV to about 5 kV is applied to the capillary 16 to promote formation of negatively-charged spray droplets 22. The voltage may be applied using a voltage source (not shown) electrically connected to the metal capillary 16. A nebulizer gas 24 may be passed through the tube 18 in a direction concurrent with the flow of the solution 20 to assist in the nebulization and evaporation of the solvent from the spray droplets 22. In an embodiment of the present invention, the nebulizer gas 24 may be warmed (e.g., to a temperature of about 85° C.) to promote rapid evaporation of the solvent and desolvation of the precursor ions and other reaction products in the spray droplets 22. In another embodiment, the environment of the spray droplets 22 may be maintained at an elevated temperature. In other embodiments, the droplets 22 may evaporate under ambient conditions at a pressure of approximately 1 atm (i.e., about $10^5$ Pa).

The solvent evaporation from the charged droplets 22 proceeds until all of the water and organic solvent is removed, following processes which are well known, such as those described in the following articles: (1) G. D. Wang, R. B. Cole. *Analytica Chimica Acta,* 406(1) (2000) 53-65; (2) P. Kebarle. *Journal of Mass Spectrometry,* 35(7) (2000) 804-817; (3) P. Kebarle, M. Peschke. *Analytica Chimica Acta,* 406(1) (2000) 11-35; and (4) M. Labowsky, J. B. Fenn, J. F. de la Mora. *Analytica Chim. Acta,* 406(1) (2000) 105-118, each of which is incorporated by reference herein in its entirety. After the water and organic solvent has been removed, desolvated negative and positive ions, ion pairs, and salt clusters remain as a vapor phase 26.

The second stage of the process may be carried out in an electrostatic ion separation device, such as mass spectrometer 14 of FIG. 1. In an embodiment of the invention, the mass spectrometer 14 is a bench-top mass spectrometer. The mass spectrometer 14 is equipped with aperture plate 28 and metal plate 30 which define a skimmer region 32 between them, which may be evacuated to a substantially constant pressure of about $10^2$ Pa by means known in the art. The plates 28 and 30 are provided with respective apertures 34 and 36, through which the desolvated vapor phase 26 can be drawn. In an embodiment of the present invention, the mass spectrometer 14 includes, a first quadrupolar mass analyzer 38, a collision cell 40, and a second quadrupolar mass analyzer 42. In other embodiments, other devices capable of electromagnetically separating ions may be used in place of the first and second quadrupolar mass analyzers 38, 42. In embodiments of the invention, the first mass analyzer 38, the collision cell 40 and the second quadrupolar mass analyzer 42 may be evacuated to substantially constant pressures of about $10^{-4}$ Pa, $10^{-3}$ Pa and $10^{-4}$ Pa, respectively, by methods well known in the art.

In an embodiment of the present invention, the vapor phase 26 is pulled through the aperture 34 in the plate 28 into the skimmer region 32 by action of a positive potential applied to metal plate 30. A voltage difference of a few volts between the aperture plate 28 and metal plate 30 is typically enough to draw the negative anions into the skimmer region 32. Negative anions in the vapor phase 26 include singly deprotonated dicarboxylic acid anions $[HA]^-$, doubly deprotonated dicarboxylic acid anions $[A]^{-2}$, singly charged metal dicarboxylic acid salt anions $[A+M]^-$, and numerous dicarboxylic acid salt cluster anions. These anions exit the skimmer region 32 through the opening 36 in the metal plate 30, and enter the first quadrupolar mass analyzer 38. Positive ions (i.e., cations) in the vapor phase 26 are not attracted to the positively-charged plate 30, and either are not drawn into the skimmer region 32 or are trapped therein.

As noted above, negative ions exiting the skimmer region through aperture 36 of plate 30 are drawn into the first quadrupolar mass analyzer 38. The first quadrupolar mass analyzer 38 is operated to select only the [A+M]⁻ anions (hereinafter, "the precursor anions") from among the anions entering the first quadrupolar mass analyzer 38, using separation techniques widely known in the art. Thus, the first mass analyzer 38 functions as a filter to transmit only the selected precursor anions as a collimated beam, discarding all other anions drawn into the mass analyzer 38.

The precursor anions 44 selected by the first quadrupolar mass analyzer 38 pass into the collision cell 40. A collision gas 48 is added to the collision cell 40, providing means for dissociating the precursor ions 44 and maintaining the pressure in the collision cell 40. A collision gas used in embodiments of the present invention is typically an inert gas, such as one of the noble gases (i.e., helium, neon, argon, krypton, or xenon). Nitrogen is also sufficiently inert to be used as a collision gas. It is preferable to choose an inert gas that has a high atomic or molecular mass (e.g., argon or xenon), because the high mass maximizes the fraction of collision energy converted into vibrational excitation of the colliding metal ion. In an embodiment of the process of the present invention, the collision gas is argon.

Voltages are applied to the opposite ends 48, 50 of the collision cell 40 to draw the precursor anions through the collision cell 40, with the voltage at end 50 being slightly positive relative to the voltage at end 48. In accordance with known techniques of gas-phase chemistry, the physical length of the collision cell 40 may be selected to be greater than the mean free path of the precursor anions, which depends on the size of the precursor anions and the pressure of the collision gas 46.

Without being bound by theory, it is believed that the precursor anions 44 undergo inelastic collisions with gas molecules in the collision cell 40 leading to an exchange of kinetic energy with internal rotational and vibrational energy within the anions 44. It is further believed that a fraction of the precursor anions 44 thus achieve a vibrationally excited state exceeding a threshold dissociation energy ($\Delta E_1$), causing the precursor anions 44 to dissociate. The immediate products of the precursor dissociation include carbon dioxide and an intermediate metal complex anion, which is either weakly bound or metastable so that it further dissociates with a threshold energy ($\Delta E_2$), yielding a monatomic metal anion (M) as a product. This dissociation process; known as "collision-induced dissociation" (CID) is depicted in equations 1 and 2 of Dissociation Scheme 1, below, for the specific case of a singly-charged metal oxalate salt anion.

DISSOCIATION SCHEME 1

(1)

(2)

The metal anions and any undissociated precursor anions pass from the collision cell 40 into the second quadrupolar mass analyzer 42. The second analyzer 42 selects only the metal anions and passes them through the mass analyzer 42 as a collimated anion beam 52. The metal anions in the beam 52 have low kinetic energies, and can be transmitted or stored for various applications, as described in Examples 1-4, hereinbelow. A number of monoatomic metal anions may group together to form nanocluster metal anions, which would also be present in the collimated beam 52.

Demonstrating the production of gas-phase metal anions by a process such as that described above, FIGS. 2-8 are graphs of mass spectra of product ions obtained by CID of singly-charged metal dicarboxylic acid salts. CID mass spectra were recorded using a Micromass™ (Beverly, Mass.) Quattro I triple quadrupolar mass spectrometer equipped with an ESI source. Samples were infused into the ESI source as acetonitrile/water (50:50) or as methanol/water (50:50) solutions at a rate of 5 μL/min. The ESI source temperature was held at 85° C. The argon gas pressure in the hexapolar collision cell was adjusted to attenuate precursor ion transmission by 50 percent. In-source fragmentation was used to optimize the production of the desired precursor anions. Typical ESI source (S) and collision (C) voltage settings that were used are summarized in Table 1. In practice, the ESI source (S) and collision (C) voltages can be varied over a wide range, and one having ordinary knowledge of mass spectrometric techniques, and given the present disclosure, would understand how to adjust these settings to maximize the abundance of the gaseous metal anions that are generated.

TABLE 1

| FIG. No | Metal (M) | Diacid (A) | S (V) | C (V) |
|---------|-----------|------------|-------|-------|
| 2 | Na | oxalic | 85 | 25 |
| 3 | K | oxalic | 100 | 25 |
| 4 | Cs | oxalic | 47 | 15 |
| 5 | Ag | oxalic | 28 | 15 |
| 6 | K | succinic | 25 | 40 |
| 7 | K | fumaric | 55 | 30 |
| 8 | K | maleic | 152 | 30 |

Figure 2:
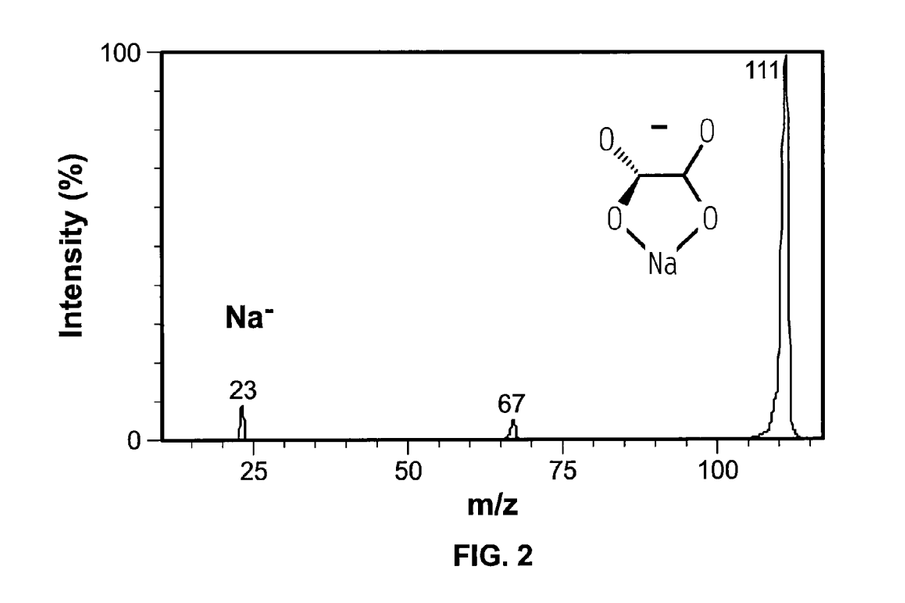
FIG. 2 is a graph of a collision-induced dissociation (CID) spectrum of substances derived from sodium oxalate by a process according to an embodiment of the present invention.
Figure 3:
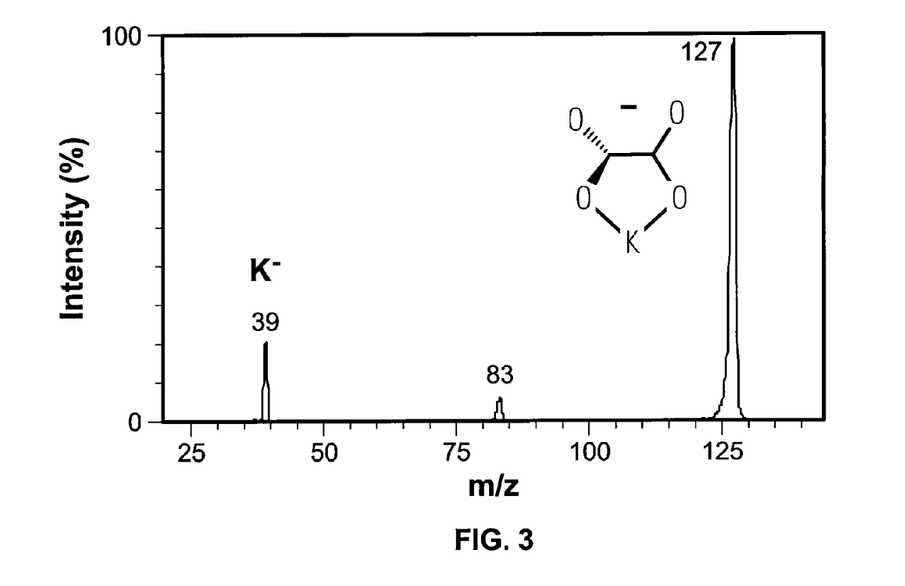
FIG. 3 is a graph of a collision-induced dissociation (CID) spectrum of substances derived from potassium oxalate by a process according to an embodiment of the present invention.
Figure 4:
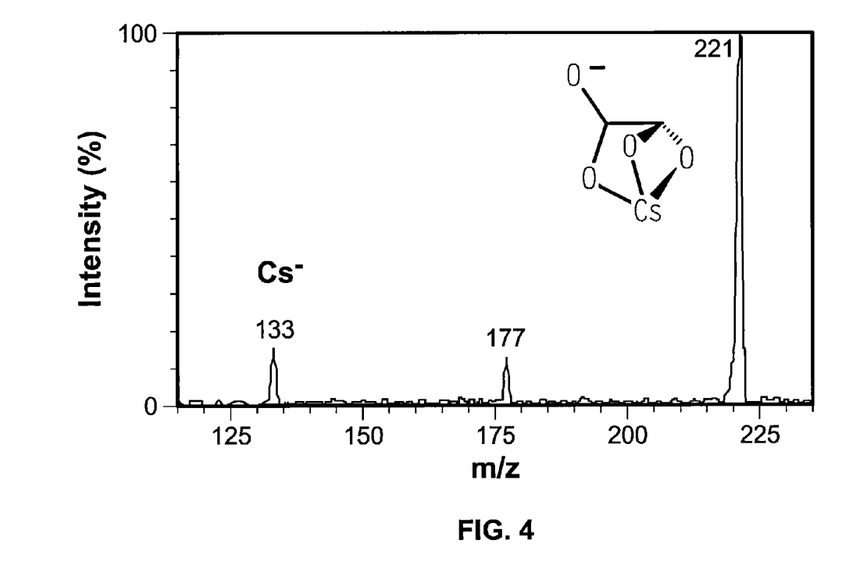
FIG. 4 is a graph of a collision-induced dissociation (CID) spectrum of substances derived from cesium oxalate by a process according to an embodiment of the present invention.
Figure 5:
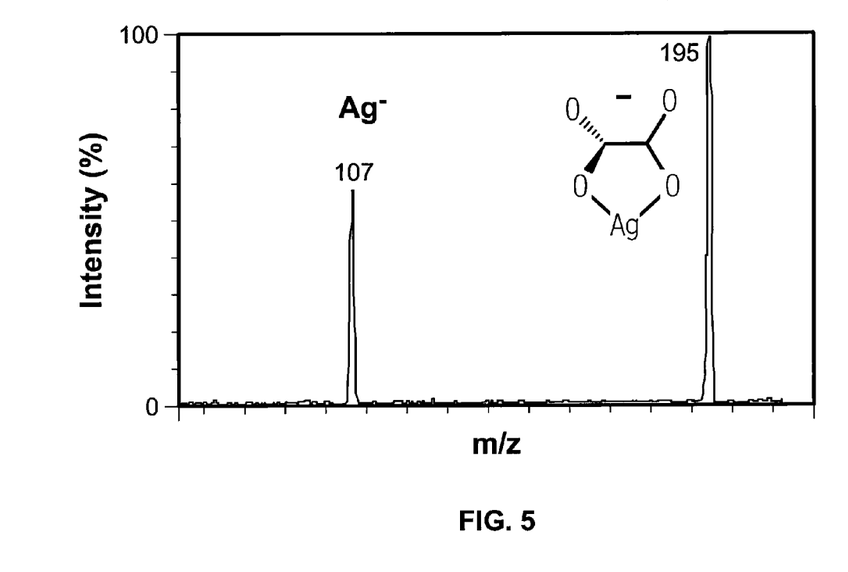
FIG. 5 is a graph of a collision-induced dissociation (CID) spectrum of substances derived from silver oxalate by a process according to an embodiment of the present invention.

FIGS. 2-5 show examples of product ion mass spectra obtained after CID of specific metal oxalate anion precursors, which had been selected in the first quadrupolar mass analyzer 38, in which:

FIG. 2 is a graph of a CID spectrum of m/z 111 derived from sodium oxalate, wherein the peak at m/z 23 represents the gas-phase Na⁻ anion;

FIG. 3 is a graph of a CID spectrum of m/z 127 derived from potassium oxalate, wherein the peak at m/z 39 represents the gas-phase K⁻ anion;

FIG. 4 is a graph of a CID spectrum of m/z 221 derived from cesium oxalate; wherein the peak at m/z 133 represents the gas-phase Cs⁻ anion; and FIG. 5 is a graph of a CID spectrum of m/z 195 derived from silver oxalate, wherein the peak at m/z 107 represents the gas-phase Ag⁻ anion.

Figure 6:
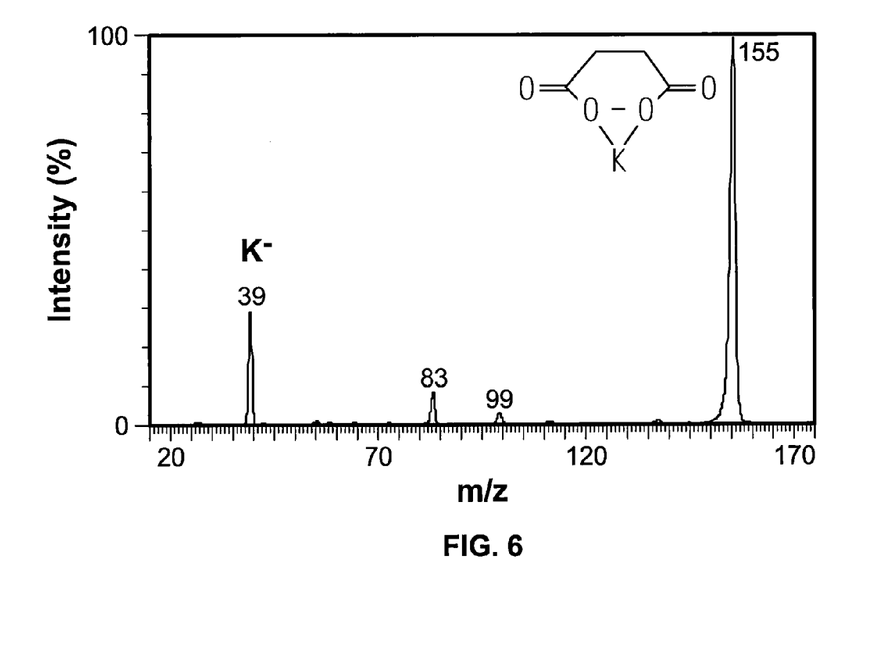
FIG. 6 is a graph of a collision-induced dissociation (CID) spectrum of substances derived from potassium succinate by a process according to an embodiment of the present invention.
Figure 7:
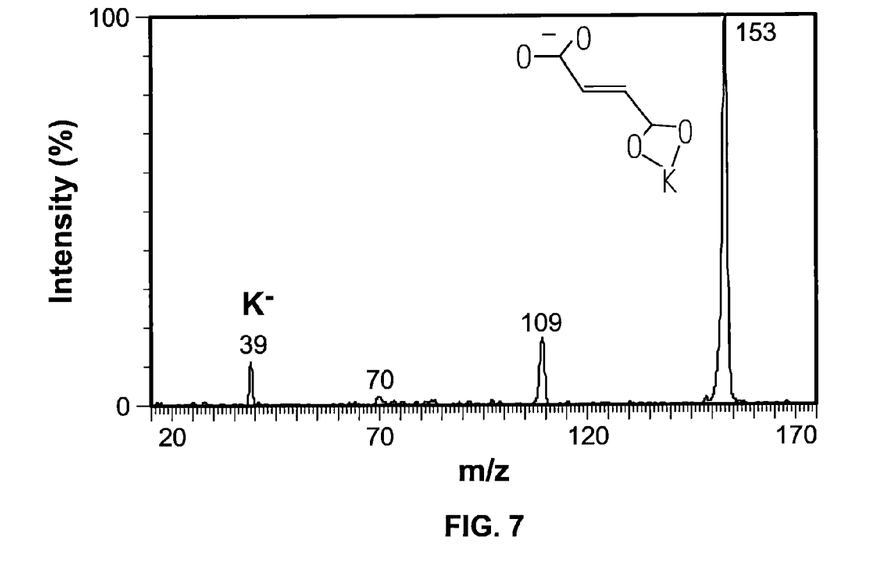
FIG. 7 is a graph of a collision-induced dissociation (CID) spectrum of substances derived from potassium fumarate by a process according to an embodiment of the present invention.
Figure 8:
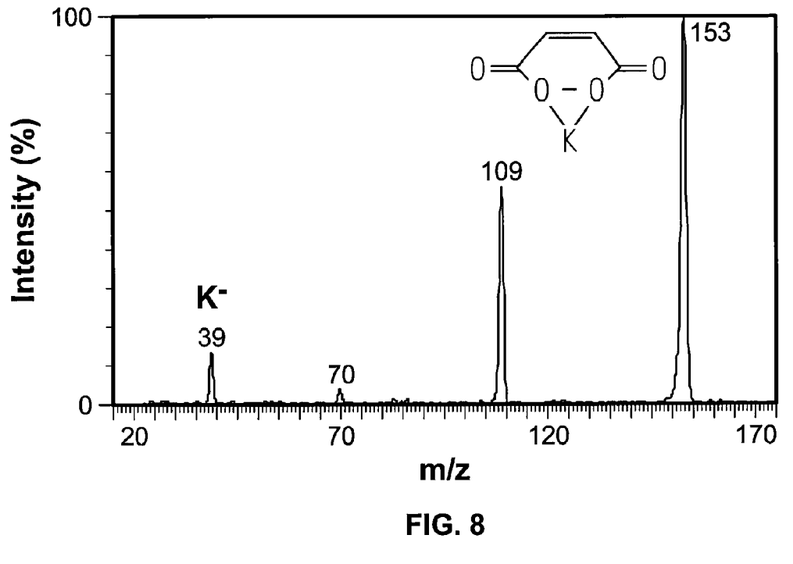
FIG. 8 is a graph of a collision-induced dissociation (CID) spectrum of substances derived from potassium maleate by a process according to an embodiment of the present invention.

FIGS. 6-8 show examples of product ion mass spectra obtained after CID of specific potassium dicarboxylate anions, other than the oxalate dianion, which had been selected in the first quadrupolar mass analyzer 38, in which:

FIG. 6 is a graph of a CID spectrum of m/z 155 derived from potassium succinate, wherein the peak at m/z 39 represents the gas-phase K⁻ anion;

FIG. 7 is a graph of a CID spectrum of m/z 153 derived from potassium fumarate, wherein the peak at m/z 39 represents the gas-phase K⁻ anion; and FIG. 8 is a graph of a CID spectrum of m/z 153 derived from potassium maleate, wherein the peak at m/z 39 represents the gas-phase K⁻ anion.

EXAMPLES

The following Examples 1-4 are intended to describe representative applications of the above-disclosed procedure for generating gas-phase metal anions. They do not encompass the entire range of such applications or of the equipment that may be used to implement them.

Example 1

Patterning of Nanomaterials

Figure 9:
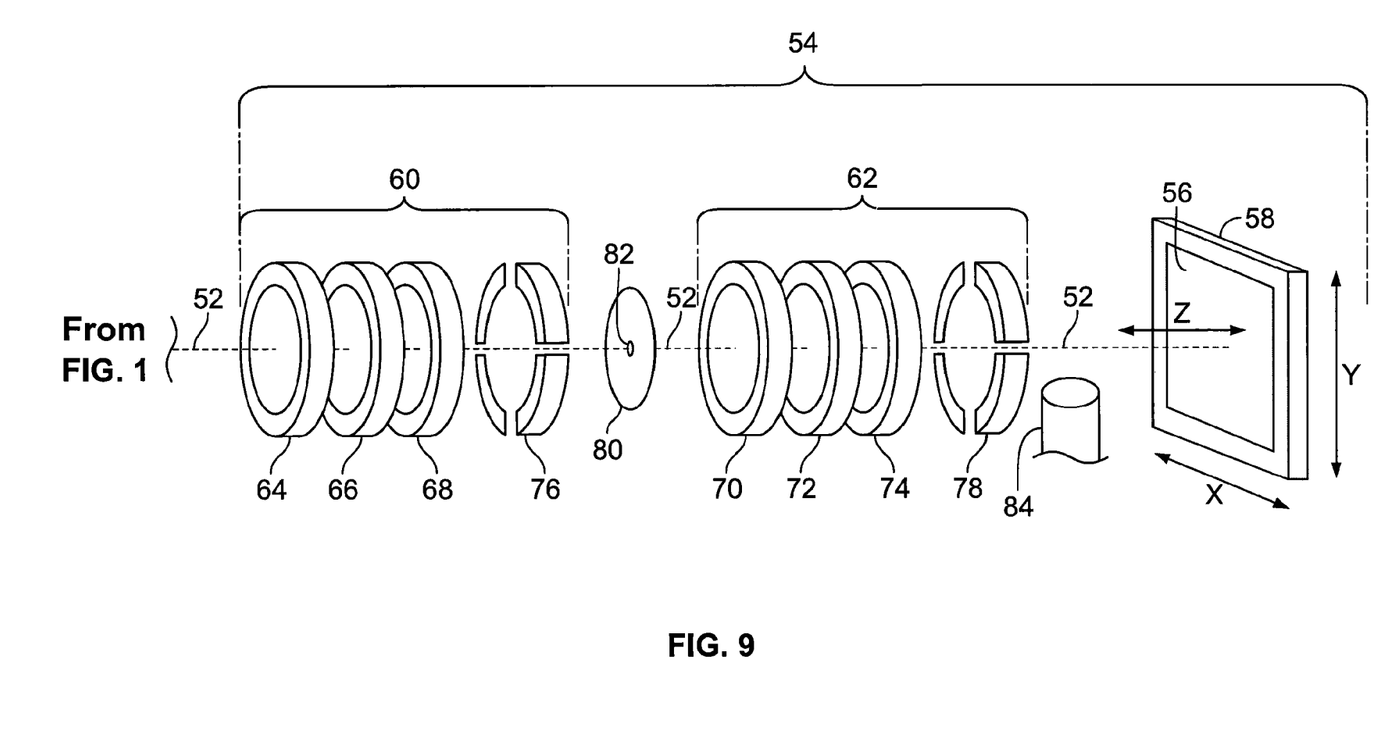
FIG. 9 is a schematic diagram of an electrostatic assembly according to an embodiment of the present invention useful for patterning nanoscale features onto a substrate in a process according to an electrostatic embodiment of the present invention.

A beam of metal anions may be used for ion-beam patterning of nanomaterials onto solid substrates to create patterned nanoscale structures using a direct-writing methodology. FIG. 9 is a schematic diagram of an ion-beam patterning assembly 54 according to an embodiment of the present invention, which may be used to transmit a metal anion beam 52 to the second surface 56 of a flat solid substrate 58. The ion-beam patterning assembly 54 may be hyphenated to the second quadrupolar mass analyzer 42 of FIG. 1 to receive the ion beam 52 emitted from the second quadrupolar mass analyzer 42.

In the present Example, the anion beam 52 emitted from the second quadrupolar mass analyzer 42 of FIG. 1 enters a series of at least two electrostatic lenses 60, 62. Each lens 60, 62 consists of three respective concentric rings 64, 66, 68, 70, 72, 74 aligned with the direction of the beam 52. Voltages may be applied individually to the concentric rings 64, 66, 68, 70, 72, 74 to collimate, guide and focus the metal anion beam 52. Each electrostatic lens assembly 62, 64 is also equipped with a respective four-fold segmented ring 76, 78 to which voltages can be applied to steer the ion beam 52 for the purpose of correcting misalignments.

Patterning of nanoscale structures typically requires rigorously clean conditions under ultra-high vacuum (UHV). Therefore, a mechanism is needed to guide the anion beam 52 into an UHV environment. The first lens 60 is separated from the adjacent lens 62 by an aperture plate 80 having a small opening 82 therethrough with a sufficiently-large diameter to allow the focused metal anion beam 52 to pass through. The aperture plate 80 also acts as a barrier to gas flow, allowing a difference in pressure to exist between the lenses 60, 62. The pressure difference may be maintained by two successive pumping stages (not shown), operating to maintain vacuum conditions in the respective lens 60, 62. The metal anion beam 52 can in this way be transmitted into a region with a different pressure than the pressure at which the metal anions in the beam 52 were formed. In an exemplary embodiment, the first lens 60 is held at a pressure that is about equal to that of the metal anion beam 52 (e.g., a pressure of about $10^{-4}$ Pa). The second lens 62 and other elements to the right of the aperture plate 80, as shown in FIG. 9, are maintained under an ultra-high vacuum (e.g., a pressure of $10^{-8}$ Pa). One having skill in the art will understand that FIG. 9 is a simplified schematic, and will be aware of the additional elements that may be needed to maintain the desired pressure differences across the assembly.

The second lens assembly 62 focuses the metal anion beam 52 onto the planar surface 56 of a solid substrate 58 which is fixed to an adjustable substrate mount (not shown). The substrate mount is capable of moving at least in the X and Y directions with respect to the Z direction of the intersecting anion beam 52. A shutter device 84 is also incorporated into the assembly 54 between the second lens assembly 62 and the substrate 58. The shutter device 84 functions to selectively block or deflect the metal anion beam 52 so that it intermittently impinges on the surface 56 of the substrate 58. A programmable control device (not shown) coordinates the movement of the substrate mount and the actuation of the shutter 84 so that metal from the metal anion beam 52 is deposited on the surface 56 of the substrate 58 in a predetermined pattern.

Example 2

Reagent Ions for Gas-Phase Micro-Reactors

Figure 10:
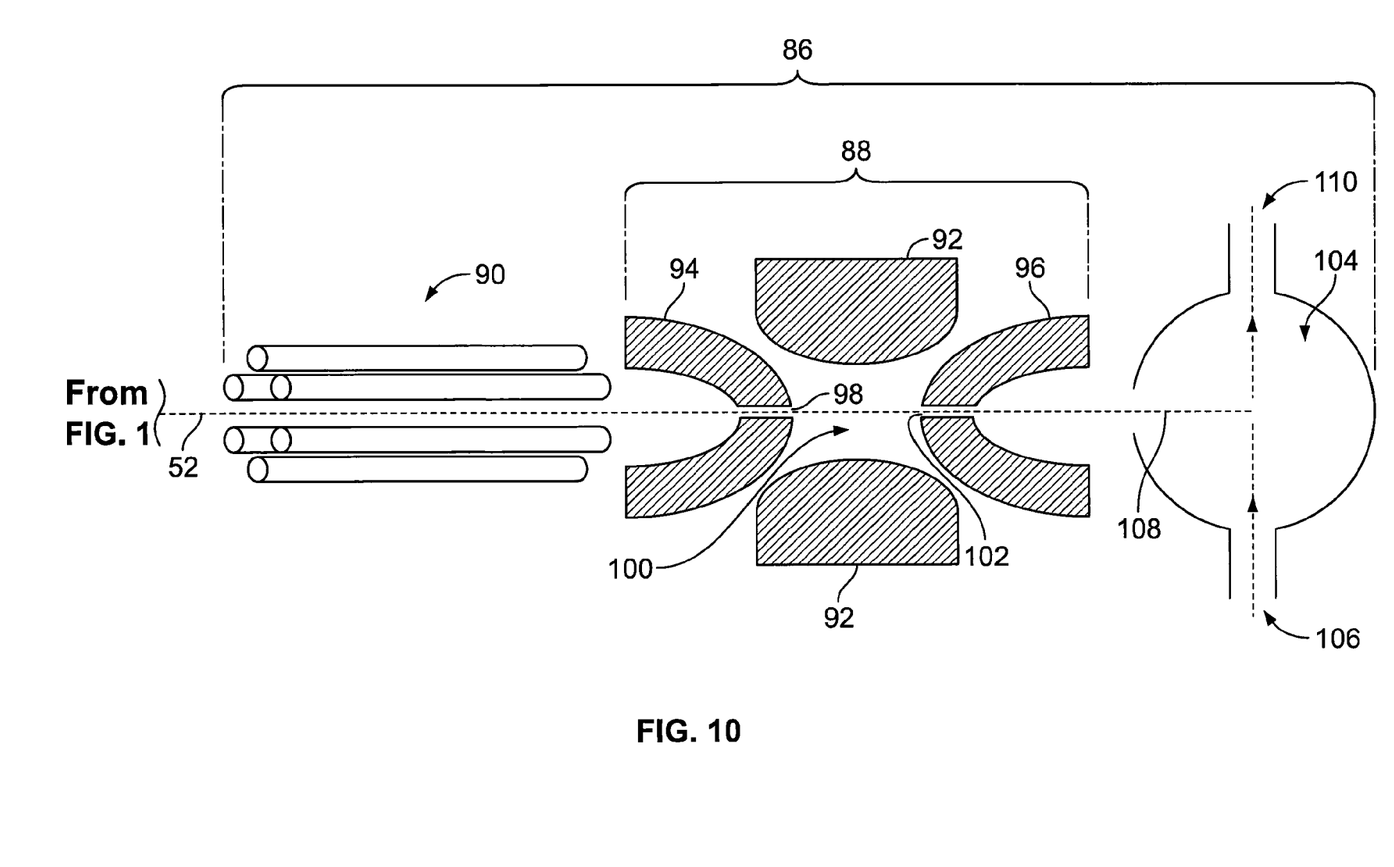
FIG. 10 is a schematic diagram of an electrostatic assembly according to an embodiment of the present invention useful for delivering monatomic metal anions to an ion trap for temporary storage in a process according to an embodiment of the present invention.

FIG. 10 is a schematic diagram of an ion trap/micro-reactor assembly 86 for delivering monatomic metal anions 52 to an ion trap 88 for temporary storage in a process according to an embodiment of the present invention. The assembly 86 can be hyphenated to the second quadrupolar mass analyzer 42 of FIG. 1 to receive the metal anion beam 52.

The ion trap/micro-reactor assembly 86 includes an ion transfer device 90 mounted downstream from the second quadrupolar mass analyzer 42 of FIG. 1. In some embodiments of the present invention, the ion transfer device 90 may be an octapolar or hexapolar device. The ion transfer device 90 guides the metal anions 52 into an ion trap 88. FIG. 10 schematically depicts a cylindrical quadrupolar ion trap 88, but other ion trapping devices may be used, such as a Penning trap, an Orbitrap™ (Thermo Fisher Scientific, Inc., Waltham, Mass.), or a massively parallel array of micofabricated quadrupolar ion traps.

The quadrupolar ion trap 88 includes a ring electrode 92 (depicted schematically in cross-section) and two end-cap electrodes 94 and 96 (depicted schematically in cross-section). Metal anions from metal anion beam 52 enter the ion trap 88 through an opening 98 in the end-cap 94. Anions within the trap 88 experience superimposed DC and RF potentials due to voltages applied to the ring electrode 92 and end-cap electrodes 94, 96. Anions are thus guided into closed stable trajectories within the interior 100 of the trap 88. A neutral buffer gas (for example helium or argon) may also be admitted into the ion trap 88 at a partial pressure of approximately 0.1 Pa to dampen ion motions by collisional cooling. The anions can thus be stored in the ion trap 88 and used later as reagents for gas-phase ion-molecule reactions.

Metal anions in this example can be ejected from the ion trap 88 and transferred to an adjacent micro-reactor cell 104 by the application of a positive potential on the exit end-cap 96. Anions will be attracted to the exit end cap 96, and a portion of them will exit through an opening 102 in the end cap 96. A gas-phase neutral analyte 106 flows into the micro-reactor cell 104, where it reacts with the ejected metal anions 108. Reaction products 110, formed by the collision of metal anions 108 with the neutral analyte 106, then exit the reactor 104, where they may be received by appropriate analytical equipment, such as a mass spectrometer (not shown).

Example 3

Electron Transfer Agents for Elucidating Protein Structure

Figure 11:
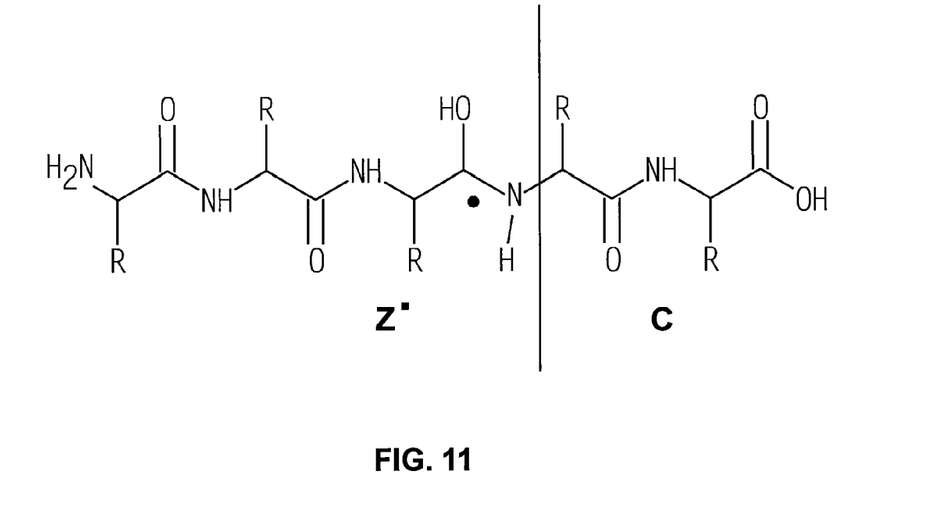
FIG. 11 is a diagram illustrating the fragmentation of a generic peptide radical to generate c and $z^{\bullet}$ products by a process according to an embodiment of the present invention.

A metal anion beam may be used to elucidate the structure of large molecules, such as proteins, through electron transfer dissociation (ETD). ETD is a process used in mass spectrometry to cause fragmentation of multiply-charged protonated cations, which often are polypeptides or proteins with structural units linked by amide bonds. ETD is an important process for protein structure elucidation, because the process cleaves many more bonds than conventional collision-activated dissociation processes. Almost all fragmentation of peptides initiated by ETD comes from one particular type of bond cleavage: the partial reduction of polypeptide cations $[R+nH]^{n+}$ to form radical cations of the form $[R+nH]^{(n-1)+\bullet}$. Dissociation of these radical cations produces a complementary series of c and z• type ions (e.g., as shown in FIG. 11) as result of homolytic cleavage of $C-N_\alpha$ bonds. Types c and z• ions are dissociation products formed by breaking a nitrogen-alpha carbon bond in the backbone of a polypeptide chain. The dissociation of a peptide radical to generate c and z• type products adjacent to the radical site is depicted more explicitly in FIG. 11. The use of ETD processes for characterizing peptides and proteins are described in the following references: (5) Syka, J. E., et al., Peptide and protein sequence analysis by electron transfer dissociation mass spectrometry, *Proc. Natl. Acad. Sci. U.S.A.*, 101(26) (2004) 9528-33; and (6) Coon, J. J., et al., Anion dependence in the partitioning between proton and electron transfer in ion/ion interactions, *Int. J. Mass Spectrom.* 236 (2004) 33-42, each of which is incorporated by reference herein in its entirety.

In a typical ETD process an appropriate reagent capable of capturing electrons (e.g., fluoranthene) is introduced into a chemical ionization (CI) source and converted into a radical anion $(A^{-\bullet})$ by a process of low energy electron capture. Typically, anion generation in a CI source requires that the precursor be sufficiently volatile to occupy the vapor phase. Formation of metal anions in a CI source at low temperature has been difficult to accomplish due to the low volatility of most metals. The generation of metal anions in a process such as that discussed with respect to FIG. 1 circumvents the problems associated with the low volatility of metals, because the precursor is introduced as a solution-phase metal acid salt.

A typical ETD process involving an anion $(A^-)$ is described in equations (3) and (4) below:

$$[R+nH]^{n+} + A^{-\bullet} \rightarrow [R+nH]^{(n-1)+\bullet} + A \quad (3)$$

$$[R+nH]^{(n-1)+\bullet} \rightarrow \text{dissociation products of type } c \text{ and } z\bullet \quad (4)$$

In an embodiment of the present invention, beams of gas-phase monatomic metal anions $(M^-)$ may be used to derive information about the primary structure of peptides by reacting $M^-$ with protonated peptide ions in an ETD-type process. In this process, metal anion beams produced as described with respect to FIG. 1 would be directed onto a sample of a protein or other large molecule (e.g., using electrostatic lenses such as those discussed with respect to FIGS. 9 and 10), and the desorbed fragments of the sample would be guided (e.g., by a carrier gas) into an appropriate analytical device. In some embodiments, an assembly such as assembly 86 of FIG. 10 would be used to analyze a sample of a volatile large molecule in the gas phase. Analytical methods of the present invention which utilize beams of gas-phase metal anions are referred to herein as metal-anion assisted dissociation (MAAD) processes.

The MAAD process involving a metal anion $(M^-)$ is described in the equations (5) and (6), below:

$$[R+nH]^{n+} + M^{-\bullet} \rightarrow [R+nH]^{(n-1)+\bullet} + M^\bullet \quad (5)$$

$$[R+nH]^{(n-1)+\bullet} \rightarrow \text{dissociation products of type } c \text{ and } z\bullet \quad (6)$$

In contrast to conventional ETD, MAAD produces additional diagnostic information about peptide structure via additional reactions between the peptide cation and a neutral metal radical, as described in equations (7) and (8), below:

$$[R+nH]^{n+} + M^\bullet \rightarrow [R+nH]^{(n-1)+\bullet} + M^+ \quad (7)$$

$$[R+nH]^{(n-1)+\bullet} + M^\bullet \rightarrow [R+nH]^{(n-2)+} + M^+ \quad (8)$$

Several non-metallic neutral molecules or radicals have been used previously as precursors to generate ETD reagents. A comparison of the physical properties and ETD efficacy of these reagents is instructive in understanding the MAAD process. The electron affinities (EA) of several typical precursors for ETD are provided in Table 2, below, along with ratings of the resulting transfer agents' efficacy in producing ETD products from a protonated peptide cation. Data in Table 1 were taken from (7) Gunawardena, H. P., et al., *J. Am. Chem. Soc.* 127(36) (2005) 12627. It may be noted that the precursor molecules (or atoms) listed in Table 1 have electron affinities that vary in the range of about 5 to about 113 kcal/mol. The efficacy of electron transfer varies in a range of 0% to about 49%. Thus, Table 1 shows that there is a striking loss of efficacy for precursors with electron affinities greater than approximately 60 kcal/mol. Precursors having low electron affinities show a trend toward higher transfer efficacies.

TABLE 2

| Reagent | EA (kcal/mol) | % ETD |
| --- | --- | --- |
| norbornodiene | 5.6 | 7.2 |
| cis-stilbene | 10.4 | 9.8 |
| $O_2$ | 10.4 | 4.9 |
| $CS_2$ | 11.8 | <0.01 |
| azobenzene | 13.1 | 48.8 |
| fluoranthene | 14.5 | 37.4 |
| perylene | 22.4 | 20.9 |
| nitrobenzene | 23.0 | 14.7 |
| $SF_6$ | 24.2 | <0.01 |
| $SO_2$ | 25.5 | 30.1 |
| m-dinitrobenzene | 38.3 | 26.6 |
| o-dinitrobenzene | 38.3 | 17.2 |
| $S_2O$ | 43.3 | 7.3 |
| $SO_3$ | 43.8 | <0.01 |
| p-dinitrobenzene | 46.1 | 16.4 |
| $S_3$ | 48.3 | 7.0 |
| $O_3$ | 48.5 | 4.8 |
| $NO_2$* | 52.4 | 8.5 |
| 1,3,5-trinitrobenzene | 60.6 | 7.9 |
| $CO_3$ | 62.0 | <0.01 |
| I* | 70.6 | <0.01 |
| $CH_3COO$* | 77.4 | <0.01 |
| $NO_3$* | 90.8 | <0.01 |
| $H_2PO_4$ | 105.4 | <0.01 |
| $SF_5$* | 108.4 | <0.01 |
| $HSO_4$ | 109.5$^j$ | <0.01 |
| picric acid | 113.1 | <0.01 |

Table 3, below, lists electron affinities of several exemplary metals that may be used as precursors for generating metal anions by the processes described herein as embodiments of the present invention. These metals have low electron affinities that fall within a range of about 10 to about 30 kcal/mol. Such values are consistent with the production of metal anions having high transfer efficacies.

TABLE 3

| Reagent | EA (kcal/mol) |
|---|---|
| Li | 14.3 |
| Na | 12.6 |
| K | 11.6 |
| Rb | 11.2 |
| Cs | 10.9 |
| Ag | 30.0 |

Until the present disclosure, the art did not include metal anion beam sources that could be easily integrated into ETD experiments with existing benchtop equipment. However, based on the evaluation of the data of Table 2 discussed above, it can be reliably predicted that such metal anions can beneficially be used in ETD methods.

There is other strong evidence that metal anions are excellent electron transfer reagents. It is known in the art that gas-phase cesium atoms (in the absence of any ionization method) are capable of undergoing ETD reactions with protonated peptide cations. If transfer of an electron from a neutral metal atom is facile, then the transfer of an electron from the corresponding metal anion should be expected to be extremely efficient, because of the low binding energies of surplus electrons in metal anions.

Further, the use of metal anions in ETD would be more effective than the use of the anions (A⁻) of the molecules (or atoms) of Table 2. Some of the anions that are listed in Table 2 have a limited capability to undergo ion-ion reactions involving electron transfer, because they can also participate in an energetically more favorable process of proton transfer, in which the protonated cation transfers $H^+$ to the approaching anion to neutralize it. The competing proton transfer process is described in the equation below:

$$[R+nH]^{n+} + A^- \rightarrow [R+(n-1)H]^{(n-1)+} + AH \qquad (9)$$

In this competing, and undesirable process, the anion functions as a strong base with high proton affinity instead of functioning as a reducing agent. Some anions display a dual behavior in which both proton and electron transfer occurs. Gas-phase metal anions are not known to function as strong bases with a high proton affinity; therefore, the competing process of proton transfer is unlikely to reduce their efficacy in ETD reactions. A neutral hydride, such as CsH, that might be generated by a proton transfer to a $Cs^-$ ion would be expected to be only weakly bound in its ground state and susceptible to dissociation, forming $Cs^+$ and $H^-$.

Persons having ordinary skill in the art of mass spectrometric techniques, given the present disclosure, will understand how the gas-phase metal anion beams of the present invention could be used in other analytical techniques. For example, such beams can be used as a primary ion source for secondary ion microscopy, which is a nanoscale imaging method used to characterize inorganic materials and biological tissue samples.

Example 4

Metal Anions for Surface Treatment of Biomaterials

Methods for the surface treatment of biomaterials are important for improving the function and biocompatibility of medical devices such as orthopedic prostheses, catheters, and orthodontic appliances. Ion beam-based surface treatment processes provide a variety of beneficial surface property modifications without impacting the bulk properties of the devices. Ion beams with high kinetic energy interact with surfaces by a mechanism of ion implantation, which heats surfaces locally and transfers large amounts of energy, which can degrade the surfaces or impart other undesirable properties thereto. In contrast, embodiments of the present invention produce metal anion beams (such as metal anion beam 52 of FIG. 1) having low kinetic energies, which can be used to modify delicate biomaterial surfaces without significant local heating.

In an embodiment of the present invention, metal anion beams having low kinetic energy are used to form infection-resistant coatings on implantable medical devices. For example, treatment of surfaces with silver has been demonstrated to be safe and effective in inhibiting microbial growth. Metal anion beams produced by processes according to embodiments of the present invention may be used to treat substrate surfaces of biomedical implants with silver or other metals.

Figure 12:
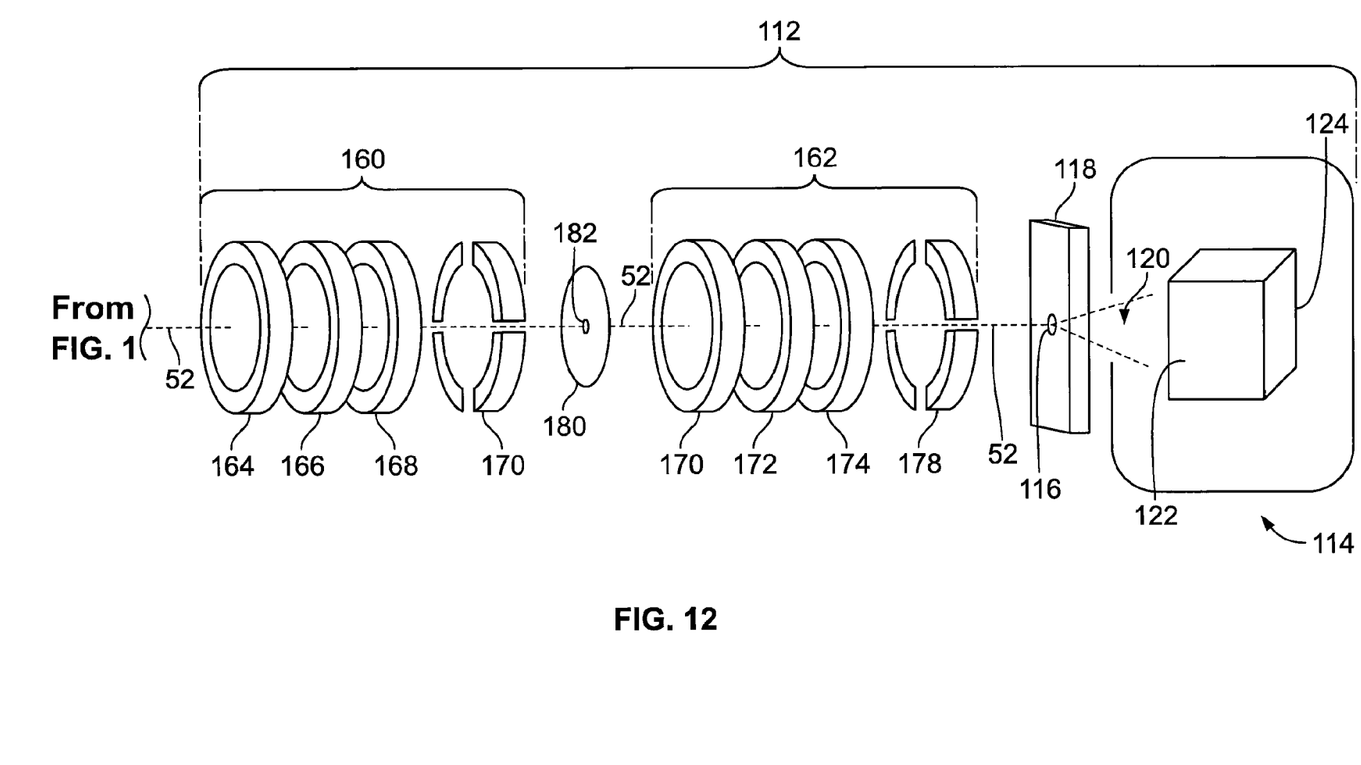
FIG. 12 is a schematic diagram of an electrostatic assembly according to an embodiment of the present invention useful for delivering monatomic metal anions to an ultra-high vacuum deposition chamber in a process according to an embodiment of the present invention.

FIG. 12 is a schematic diagram of a metal anion deposition assembly 112 according to an embodiment of the present invention for delivering monatomic metal anions to an ultra-high vacuum deposition chamber. The assembly 112 can be hyphenated to the output anion beam 52 of FIG. 1 to guide the metal anions into a deposition chamber 114 under ultra-high vacuum.

In many respects, the metal anion deposition assembly 112 is similar to the ion-beam patterning assembly 54 of FIG. 9, which is discussed in Example 1. Elements of FIG. 12 that have counterparts in FIG. 9 are shown with the same reference numbers used for those elements in FIG. 9, incremented by 100. A more detailed description of such elements may be found in the discussion of Example 1, above.

In the metal anion deposition assembly 112, voltages are applied to the concentric rings 170, 172, 174 and the four-fold segmented ring 178 of the lens 162 so as to focus the anion beam 52 so that it passes through an opening 116 in an aperture plate 118 into the deposition chamber 114. The anion beam 52 diverges after passing through the aperture 116 forming a defocused anion beam 120 so that the anions will be deposited uniformly over a wide area on the surface 122 of biomedical device 124. The biomedical device 124 will preferably be connected to a voltage source (not shown) that imparts a small positive potential to the biomedical device 124, attracting the metal anions to its surface 122. The medical device 120 might also be mounted on a rotating stage (not shown) that allows the three-dimensional object 124 to be more uniformly exposed to the defocused anion beam 120.

It should be understood that the embodiments described herein are merely exemplary and that a person skilled in the art may make many variations and modifications thereto without departing from the spirit and scope of the present invention without departing from the spirit and scope of the invention as defined in the claims below.

We claim:

1. A method of producing gas-phase metal anions, comprising the steps of:
   generating a spray of negatively-charged droplets [22] from a solution [20] including metal salts of dicarboxylic acids dissolved in a solvent, thereby producing metal cations and anions including metal dicarboxylate anions in said negatively-charged droplets [22];
   evaporating the solvent, thereby producing gas-phase unsolvated metal cations [26] and unsolvated anions [26] including unsolvated metal dicarboxylate anions [44];
   electromagnetically separating the unsolvated metal dicarboxylate anions from others of the unsolvated anions [26] and the unsolvated metal cations [26];

colliding the unsolvated metal dicarboxylate anions [44] with a non-reactive collision gas [46], thereby causing at least a portion of the unsolvated metal dicarboxylate anions [44] to dissociate into gas-phase metal anions and carbon compounds; and electromagnetically isolating the metal anions.

2. The method of claim 1, further including the step of electromagnetically collimating the gas-phase metal anions into a beam [52] of the gas-phase metal anions.

3. The method of claim 1, wherein the metal is selected from the group of metals that form monovalent cations in aqueous solution with dicarboxylic acids.

4. The method of claim 1, wherein the metal is selected from the group consisting of sodium, potassium, cesium, silver, copper, cobalt, gold, thallium, gallium, and indium.

5. The method of claim 1, wherein the dicarboxylic acid is selected from the group consisting of oxalic acid, maleic acid, fumaric acid, succinic acid, malonic acid, malic acids, tartaric acids, glutamic acids and aspartic acids.

6. The method of claim 1, wherein the solvent is selected from the group consisting of polar solvents.

7. The method of claim 6, wherein the solvent is selected from the group consisting of acetonitrile, methanol, water and mixtures thereof.

8. The method of claim 1, wherein the collision gas [46] is selected from the group consisting of helium, neon, argon, krypton, xenon and nitrogen.

9. The method of claim 1, wherein said generating step includes the step of passing the solution through a metal capillary [16] held at a high electrical potential.

10. The method of claim 9, wherein at least part of the metal capillary [16] is surrounded by a tube [18] and said evaporating step includes passing a gas through the tube [18], thus promoting desolvation of said anions and cations.

11. The method of claim 1, wherein said separating step is performed using a first electromagnetic means [38] and said isolating step is performed using a second electromagnetic means [42].

12. The method of claim 11, wherein at least one of said first and second electromagnetic means [38, 42] includes a mass analyzer.

13. The method of claim 11, wherein at least one of said first and second electromagnetic means [38, 42] includes a quadrupole mass spectrometer.

14. The method of claim 13, wherein said quadrupole mass spectrometer is a bench-scale quadrupole mass spectrometer.

15. The method of claim 1, wherein said separating step includes the step of separating the unsolvated metal cations [26] from the unsolvated anions [26], followed by the step of separating the unsolvated metal dicarboxylate anions [44] from the others of the unsolvated anions [26].

* * * * *